United States Patent [19]

Fauchere et al.

[11] Patent Number: 5,409,899

[45] Date of Patent: Apr. 25, 1995

[54] PSEUDOPEPTIDE COMPOUNDS HAVING ANTI-INFLAMMATORY ACTIVITY

[75] Inventors: Jean-Luc Fauchere, Saint-Cloud; Christophe Thurieau, Boulogne Sur Seine; Emmanuel Canet, Paris, all of France

[73] Assignee: Adir Et Compagnie, Courbevoie, France

[21] Appl. No.: 6,151

[22] Filed: Jan. 13, 1993

[30] Foreign Application Priority Data

Jan. 17, 1992 [FR] France ................... 92 00438

[51] Int. Cl.$^6$ ............................. A61K 37/02
[52] U.S. Cl. .................... 514/15; 530/314; 530/328
[58] Field of Search ................. 530/328, 314; 514/15

[56] References Cited

FOREIGN PATENT DOCUMENTS 370453  3/1990  European Pat. Off. ........ C07K 7/18

OTHER PUBLICATIONS

Proc. Soc. Exp. Biol. Med., 3, pp. 544–547 (1960)... the Winter reference.

Goodman and Gilman's Pharmacological Basis of Therapeutics, Eighth Edition, p. 590 (1990).
Pharmacological Reviews, vol. 32, No. 1, pp. 1–46 (1980).
Pharmacological reviews, vol. 44, No. 1, pp. 1–80 (1992).
Ann. Rev. Immunol., 6, pp. 49–83 (1988).
Allergy, 48, pp. 217–225 (1993).
The Lancet, vol. 338, pp. 287–288 (1991).
The Lancet, Sep. 23, 1978, pp. 663–665 (1978).
Thorax, 47, pp. 979–983 (1992).
Clin. Pharmacol. Ther., vol. 44, No. 6, pp. 613–621 (1988).
Annual Review of Medicine, vol. 22, pp. 63–84 (1971).

*Primary Examiner*—Robert J. Hill, Jr.
*Assistant Examiner*—David Lukton
*Attorney, Agent, or Firm*—Gordon W. Hueschen

[57] ABSTRACT

Compound of formula:

G-Arg-Pro-Hyp-Gly-Thia-Ser-Tic-Oic-Arg-OH where G, Arg, Pro, Hyp, Gly, Thia, Ser, Tic and Oic are defined in the description.

Medicinal products.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide

```
( i x ) FEATURE:
         ( A ) NAME/KEY: Modified-site
         ( B ) LOCATION: 1
         ( D ) OTHER INFORMATION: /label=G ( i x ) FEATURE:
         ( A ) NAME/KEY: Modified-site
         ( B ) LOCATION: 4
         ( D ) OTHER INFORMATION: /label=Hyp ( i x ) FEATURE:
         ( A ) NAME/KEY: Modified-site
         ( B ) LOCATION: 6
         ( D ) OTHER INFORMATION: /label=Thia ( i x ) FEATURE:
         ( A ) NAME/KEY: Modified-site
         ( B ) LOCATION: 8
         ( D ) OTHER INFORMATION: /note="(D)Tic"

( i x ) FEATURE:
         ( A ) NAME/KEY: Modified-site
         ( B ) LOCATION: 9
         ( D ) OTHER INFORMATION: /label=Oic ( i x ) FEATURE:
         ( A ) NAME/KEY: Modified-site
         ( B ) LOCATION: 11
         ( D ) OTHER INFORMATION: /note="OH trifluoroacetate"

( x i ) SEQUENCE DESCRIPTION: SEQ ID NO:1:

Xaa  Arg  Pro  Xaa  Gly  Xaa  Ser  Xaa  Xaa  Arg  Xaa
 1                  5                        10
```

PSEUDOPEPTIDE COMPOUNDS HAVING ANTI-INFLAMMATORY ACTIVITY

The present invention relates to new pseudopeptide compounds having bradykinin-antagonist activity.

Bradykinin, a natural nonapeptide, is known as a mediator of inflammatory and painful reactions, as well as in hypotensive states.

Bradykinin has, in addition, contractive effects on smooth muscle, especially that of the trachea, uterus or intestine. In clinical medicine, bradykinin has been implicated in the physiopathology of shock states, inflammatory reactions, asthma and bronchial hyperreactivity, allergic or viral rhinitis, pancreatitis, arthritis, postgastrectomy dumping syndrome, psoriasis, hereditary angioneurotic edema and migraine.

Application EP 0,370,453 describes bradykinin antagonists having a pseudopeptide structure which are of the formula:

A-B-C-E-F-K-(D)Tic-G-M-F-I and among these the decapeptide of formula:

H-(D)Arg-Arg-Pro-Hyp-Gly-Thia-Ser-(D)Tic-Oic-Arg-OH where
Arg represents an arginyl residue,
Pro represents a prolyl residue,
Hyp represents a 4-hydroxyprolyl residue,
Gly represents a glycyl residue,
Thia represents a β-(2-thienyl)alanyl residue,
Ser represents a seryl residue,
Tic represents a tetrahydroisoquinoline-3-carbonyl residue of formula:

Oic represents an octahydroindole-2-carbonyl residue of formula:

the abbreviation (D) preceding the symbol for one of the amino acids mentioned above meaning that this amino acid has the (D) configuration. In the absence of the abbreviation (D), the amino acids are deemed to have the (L) configuration.

The present invention describes, more specifically, the nonapeptide of formula:

G-Arg-Pro-Hyp-Gly-Thia-Ser-Tic-Oic-Arg-OH where
G represents a 4-guanidinobenzoyl radical of formula:

and
Arg represents an arginyl residue,
Pro represents a prolyl residue,
Hyp represents a 4-hydroxyprolyl residue,
Gly represents a glycyl residue,
Thia represents a β-(2-thienyl)alanyl residue,
Ser represents a seryl residue,
Tic represents a 1,2,3,4-tetrahydroisoquinoline-3-carbonyl residue,
Oic represents an octahydroindole-2-carbonyl residue, each amino acid of the peptide sequence having the D or L configuration at its α carbon, its enantiomers, diastereoisomers and epimers as well as its addition salts with a pharmaceutically acceptable acid or base.

The preferred compound of the present invention is the compound of formula:

G-Arg-Pro-Hyp-Gly-Thia-Ser-(D)Tic-Oic-Arg-OH in which:
(D)Tic possesses the D configuration at its α carbon, the other amino acids of the peptide sequence possessing the L configuration at their α carbon, Hyp is of the 4R configuration and Oic is of the (2S,3aS,7aS) configuration, as well as its addition salts with a pharmaceutically acceptable acid or base.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids, and the like.

Among pharmaceutically acceptable bases, there may be mentioned, without implied limitation, sodium hydroxide, potassium hydroxide, triethylamine, tert-butylalnine, and the like.

This compound, apart from the fact of being new, is endowed with more advantageous properties than those of the preferred derivative of Application EP 0,370,453.

The novel nonapeptide structure of the product of the invention, especially the absence of an N-terminal α-amino function, provides it in vivo with greater resistance to aminopeptidases than the decapeptide structure of the preferred compound of Application EP 0,370,453.

Moreover, its nonapeptide structure endows it with 9 asymmetric centers, that is to say one asymmetric center less than in the case of the decapeptide described in Application EP 0,370,453, which represents a not insignificant advantage in an industrial synthesis.

Furthermore, in the in vitro tests carried out in order to investigate the intrinsic activity, the compound of the invention proved significantly better than the preferred product of Application EP 0,370,453.

The invention also extends to the process for preparing the compounds of invention, which may be obtained by various methods such as sequential solid-phase synthesis, the synthesis of fragments and their coupling in solution, enzymatic synthesis and genetic synthesis by cloning and expression of genes in transformed bacteria, or by various combinations of these techniques.

The general methods of solid-phase peptide synthesis have been described by B. W. ERICKSON and R. B. MERRIFIELD ("The Proteins", Solid-Phase Peptide Synthesis, 3rd edition, volume II, 257–527, 1976).

The solid-phase synthesis may be carried out on an automated apparatus which performs in a repetitive and programmable manner deprotection, coupling and washing cycles needed for the sequential introduction of the amino acids into the peptide chain. The amino acid, preferably C-terminal, is attached to a resin conventionally used for the preparation of polypeptides, preferably a polystyrene crosslinked using 0.5 to 3.0% of divinylbenzene and equipped with activated residues such as chloromethylene or hydroxymethylene which enable the first amino acid to be attached covalently to the resin. The appropriate choice of resin enables a C-terminal carboxylic acid, amide or alcohol function to be attached. The choice of coupling site of the fragments is often determined so as to minimize the risks of racemization. Three coupling sites are, for example, the C-terminal function of the proline (at position 2), of the hydroxyproline (at position 3) and of the glycine (at position 4).

The amino acids are then introduced one by one in the order determined by the operator. Each synthesis cycle corresponding to the introduction of an amino acid entails a deprotection, preferably N-terminal, of the peptide chain, successive washes designed to remove the reactants or to swell the resin, a coupling with activation of the amino acid and further washes. Each of these operations is followed by a filtration, accomplished by means of the presence of a glass sinter incorporated in the reactor in which the synthesis takes place.

The coupling reagents used are standard reagents of peptide synthesis, such as dicylohexylcarbodiimide (DCC) and hydroxybenzotriazole (HOBT) or benzotriazol-1-yloxytris (dimethylamino)phosphonium hexafluorophosphate (BOP) or alternatively diphenylphosphoryl azide (DPPA).

Activation by mixed anhydride formation is also possible.

Each amino acid is introduced into the reactor in excess (four-fold, for example) with respect to the degree of substitution of the resin, and in an approximately equivalent amount with respect to the coupling agents. The coupling reaction may be checked at each step of the synthesis by the ninhydrin reaction test described by E. KAISER et al. (Analyt. Biochem., 34, 595, 1970).

After assembly of the peptide chain on the resin, treatment with a strong acid such as trifluoroacetic acid or hydrofluoric acid in the presence of anisole, ethanedithiol or 2-methylindole serves to separate the peptide from the resin and also to free the peptide, where appropriate, from its protective groups. The compound is then purified by standard purification techniques, in particular chromatographic techniques.

The peptides of the present invention may also be obtained by the coupling in solution of selectively protected peptide fragments, which may be prepared either on a solid phase or in solution. The general methods of peptide synthesis in solution are, for example, described by F. M. FINN and K. HOFMAN (The Proteins, 3rd edition, volume II, p. 105–253, 1976). The use of protective groups and the means of taking advantage of their differential stability are similar to the solid-phase methods, except for the attachment of the peptide chain to the resin. The C-terminal carboxyl group is protected, for example, by a methyl ester or an amide function. The methods of activation during coupling are also similar to those employed in solid-phase synthesis.

In a specific process for preparing the compound of invention by sequential solid-phase synthesis, the successive amino acids are reacted with a resin substituted with Fmoc-Arg-OH to yield the assembly H-Pro-Hyp-Gly-Thia-Ser-(D)Tic-Oic-Arg-resin, which is finally reacted with G-Arg(Pmc)-OH.

The compounds of invention possess very advantageous pharmacological properties, especially bradykinin-antagonist properties, in inflammation and bronchoconstriction.

On this basis, they may be used beneficially in a number of therapeutic indications such as traumas, grazes, burns, skin eruptions, eczema, erythema, edema, sore throat, arthritis, asthma, allergies, rhinitis, anaphylactic shock, inflammations, arterial hypotension, pains, pruritus and insufficiency of spermatozoal mobility.

The subject of the present invention is also pharmaceutical compositions containing as active principle at least one compound of invention or one of its addition salts with a pharmaceutically acceptable acid or base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, preparations to be placed under the tongue, troches, suppositories, creams, ointments, skin gels, aerosols, ampoules containing preparations to be swallowed or injected, etc.

The dosage varies according to the patient's age and weight, the nature and severity of the affliction and also the administration route.

The latter can be oral, nasal, rectal or parenteral. Generally speaking, the dosage ranges between 5 $\mu$g/kg and 5 mg/kg for a treatment administered in one or several doses per 24 hours.

EXAMPLE 1:

G-Arg-Pro-Hyp-Gly-Thia-Ser-(D)Tic-Oic-Arg-OH trifluoroacetate (SEQ. ID NO.1)

The octahydroindole-2-carboxylic acid residue (Oic) is of the (2S,3aS,7aS) configuration.

The compound of Example 1 is synthesized from 2 g of a resin substituted with 0.33 mmol/g of Fmoc-Arg-OH and according to the following repetitive protocol:

| Operation no. | Function | Solvent/ Reactant | Repetition/ time |
| --- | --- | --- | --- |
| 1 | washing | DMF | 2 × 2 min |
| 2 | deprotection | 20% piperidine/DMF | 1 × 5 min |
| 3 | deprotection | 20% piperidine/DMF | 1 × 15 min |
| 4 | washing | DMF | 3 × 2 min |
| 5 | washing | dichloromethane | 3 × 2 min |
| 6 | coupling | activated protected amino acid | 1 × 90 min |
| 7 | washing | DMF | 3 × 2 min |
| 8 | washing | isopropyl | 3 × 2 min |

| Operation no. | Function | Solvent/Reactant | Repetition/time |
|---|---|---|---|
| | | -continued | |
| 9 | washing | alcohol dichloromethane | 3 × 2 min |

Each of these operations, performed in 30 ml of solvent with agitation at room temperature, is followed by filtration through a glass sinter incorporated in the glass cell (reactor) in which the synthesis progresses. The filter retains the resin to which the growing peptide chain is attached.

The chosen protected amino acids were introduced in the following order: Fmoc-Oic-OH, Fmoc-(D)Tic-OH, Fmoc-Ser(tBu)-OH, Fmoc-Thia-OH, Fmoc-Gly-OH, Fmoc-Hyp(tBU)-OH, Fmoc-Pro-OH and G-Arg(Pmc)-OH.

The activation for the purpose of coupling (operation 6) is obtained in each cycle by dissolving 4 equivalents (2.64 mmol) of the protected amino acid with 360 mg of HOBt in 30 ml of DMF, and then, after 30 minutes at room temperature, by adding 618 mg of DCC. This solution is then introduced immediately into the reaction cell with 10 ml of dichloromethane.

At the end of the eight cycles corresponding to the sequential attachment of eight amino acids, and with C-terminal arginine, a nonapeptide protected on its side chains and attached at the C-terminal position to the resin has thereby been obtained. The resin is then treated with a mixture of trifluoroacetic acid (18 ml), dichloromethane (1 ml) and anisole (1 ml) for 90 minutes at room temperature. The filtrate and the solvents used for washing the resin (3×20 ml of dichloromethane) are combined and evaporated to dryness. The product is suspended in ether, filtered off and dried, then purified by preparative HPLC on a $C_{18}$ column (internal diameter: 47 mm, length: 300 mm) and lyophilized.

Analysis of the product obtained is carried out after decomposition of the latter into amino acids by hydrolysis in 6N hydrochloric acid for 18 hours at 110° C., and quantitative assay of the amino acids obtained by HPLC. This analysis complies with the standards normally required.

EXAMPLE 2:

Pharmacological study of the compound of the invention: rabbit jugular vein: $B_2$ receptor Bradykinin produces a contraction which is inhibited by the product of Example 1. The $pA_2$ (negative logarithm of the molar concentration of the compound of the invention which necessitates a doubling of the bradykinin concentration in order to obtain the same effect) is 9.73±0.1 (n=5).

Under the same conditions, the $pA_2$ of the preferred compound of Application EP 0,370,453 is 9.23±0.45, equivalent to a significant difference in favor of the compounds of the invention.

EXAMPLE 3:

In vivo measurement of the anti-inflammatory activity of the compound of the invention The anti-inflammatory activity of the compound of the invention was measured using the model of edema of the rat's foot induced by injection of carrageenan (WINTER G. A. et al., Proc. Soc. Exp. Biol. Med., 3, 544–547, 1960).

This study is performed on male rats weighing 180–210 g in groups of 8. The compounds of the invention are administered I.V. at time 0 immediately preceding the subcutaneous injection of carrageenan into the sole of the rat's right hind foot (type IV lambda carrageenan, Sigma, 1% solution, volume injected 0.1 ml). The volume of the foot at different time-points of the experiment is measured by plethysmography. The inhibition of the edema at time 3 hours is calculated relative to a control group which has received the vehicle, and expressed as a percentage inhibition.

Under these conditions, the compound of Example 1 produces a 59% inhibition at time 3 hours at a dose of 0.1 mg/kg I.V.

EXAMPLE 4:

Pharmaceutical composition Ointment containing 5 μg/ml of the peptide of Example 1

| | |
|---|---|
| G-Arg—Pro—Hyp—Gly—Thia—Ser—(D)Tic-Oic—Arg—OH | 50 mg |
| Polyethylene glycol Q.S. | 100 ml |

Solution for injection

| | |
|---|---|
| G-Arg—Pro—Hyp—Gly—Thia—Ser—(D)Tic-Oic—Arg—OH | 0.5 mg |
| Distilled water for injections Q.S. | 25 ml |

We claim:

1. A compound selected from those of formula (I):

G-Arg-Pro-Hyp-Gly-Thia-Ser-Tic-Oic-Arg-OH (I)

wherein:
- G represents a 4-guanidinobenzoyl radical of formula:

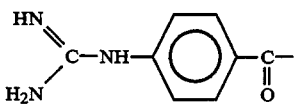

- Arg represents an (S)-arginyl residue,
- Pro represents an (S)-prolyl residue,
- Hyp represents a (4R)-hydroxyprolyl residue,
- Gly represents an (S)-glycyl residue,
- Thia represents an (S)-($\beta$-(2-thienyl)alanyl residue,
- Ser represents an (S)-seryl residue,
- Tic represents an (R)-1,2,3,4-tetrahydroisoquinoline-3-carbonyl residue, and
- Oic represents a (2S,3aS,7aS)-octahydroindole-2-carbonyl residue, and its pharmaceutically-acceptable acid or base addition salts.

2. A method for treating an animal or human living body afflicted with an inflammatory condition comprising the step of administering to the living body an effective anti-inflammatory amount of a compound of claim 1 which is effective for alleviation of said condition.

3. A pharmaceutical composition useful as an anti-inflammatory agent comprising as active principle an anti-inflammatory effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,409,899
DATED : April 25, 1995
INVENTOR(S) : Jean-Luc Fauchere, Christophe Thurieau, Emmanuel Canet It is certified that error appears in the above-indentified patent and that said Letters Patent is hereby corrected as shown below:

TITLE PAGE, ITEM [56], References Cited; FOREIGN PATENT
   DOCUMENTS; "370453 3/1990 European Pat. Off. C07K 7/18"
   should read -- 370453 5/1990 DE. Henke --
Column 2, line 45; "butylalnine" should read -- butylamine --
Column 6, line 34; start a new line with "Ointment containing 5"
Column 8, line 48; move the words "anti-inflammatory" from the
   beginning of the line and place them after the word
   "effective" to read -- effective anti-inflammatory
   amount --

Signed and Sealed this

Fourth Day of July, 1995

Attest:

BRUCE LEHMAN

Attesting Officer

Commissioner of Patents and Trademarks